United States Patent
Lowey

[11] Patent Number: 5,865,821
[45] Date of Patent: Feb. 2, 1999

[54] SUPPORT SYSTEM FOR CATHETER LEG BAG

[76] Inventor: Michael J. Lowey, 211 Linda Cove, Ft. Walton Beach, Fla. 32515

[21] Appl. No.: 859,216

[22] Filed: May 20, 1997

[51] Int. Cl.[6] ...................................................... A61F 5/44
[52] U.S. Cl. ........................................... 604/352; 604/329
[58] Field of Search .................................... 604/329, 331, 604/349, 352, 353

[56] References Cited

U.S. PATENT DOCUMENTS

| | | |
|---|---|---|
| 1,416,238 | 5/1922 | Seiler . |
| 2,133,130 | 10/1938 | Buchstein ................................ 128/349 |
| 3,897,785 | 8/1975 | Barto, Jr. ................................ 128/295 |
| 4,073,295 | 2/1978 | Laufbahn ................................ 128/295 |
| 4,173,979 | 11/1979 | Odis ....................................... 128/295 |
| 4,511,358 | 4/1985 | Johnson, Jr. et al. ................... 604/327 |

FOREIGN PATENT DOCUMENTS 3722251  1/1989  Germany ................................ 604/353

Primary Examiner—Robert A. Clarke
Attorney, Agent, or Firm—Ray F. Cox, Jr.

[57] ABSTRACT

A support system for a catheter urine collection bag comprising three circumferential straps with suitable padding and adjustable hook and loop closures. The circumferential straps are held in proximity to one another by a first longitudinal strap connecting the three on their front surfaces, and a second longitudinal control strap between the upper strap and the second strap on their rear surfaces. The longitudinal control strap acts fundamentally as a hinge between the upper two circumferential straps to prevent the circumferential straps from twisting out of position relative to one another. The second circumferential strap and the lower, third strap have loop closure material which matches hook closure material threaded through the support holes formed into the bag.

7 Claims, 4 Drawing Sheets

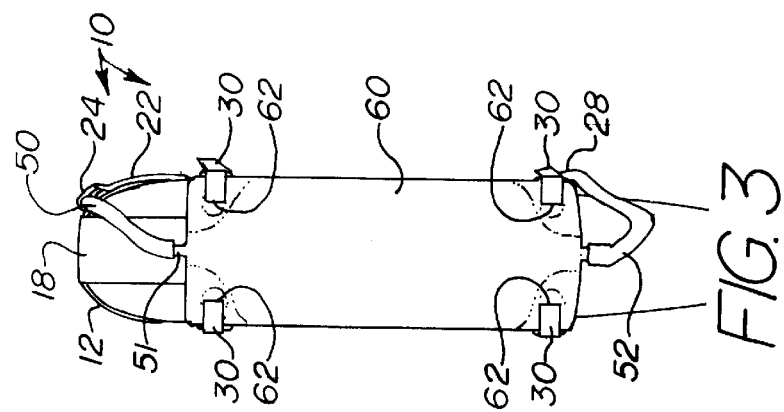
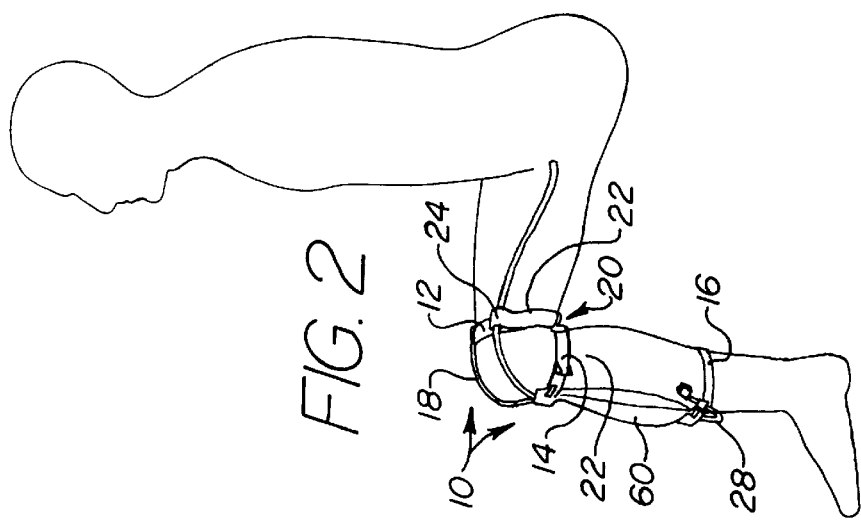
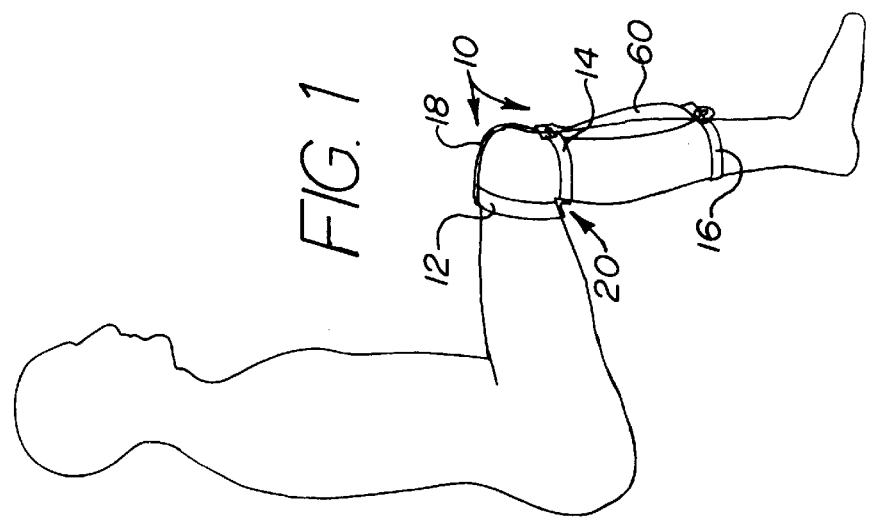

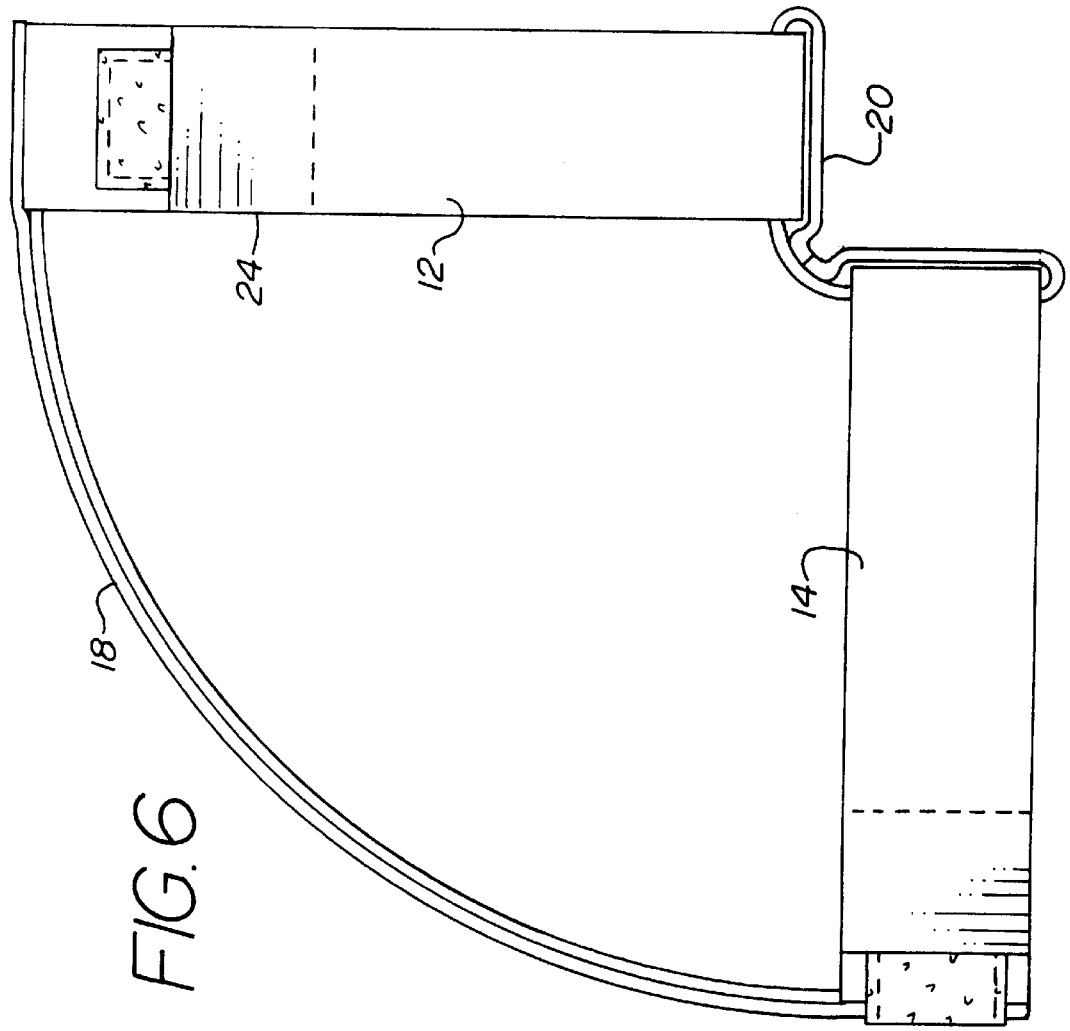

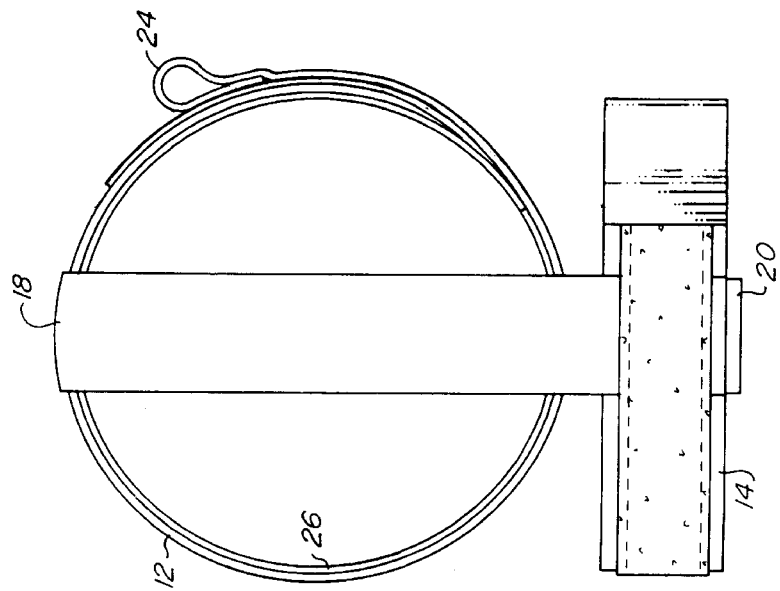
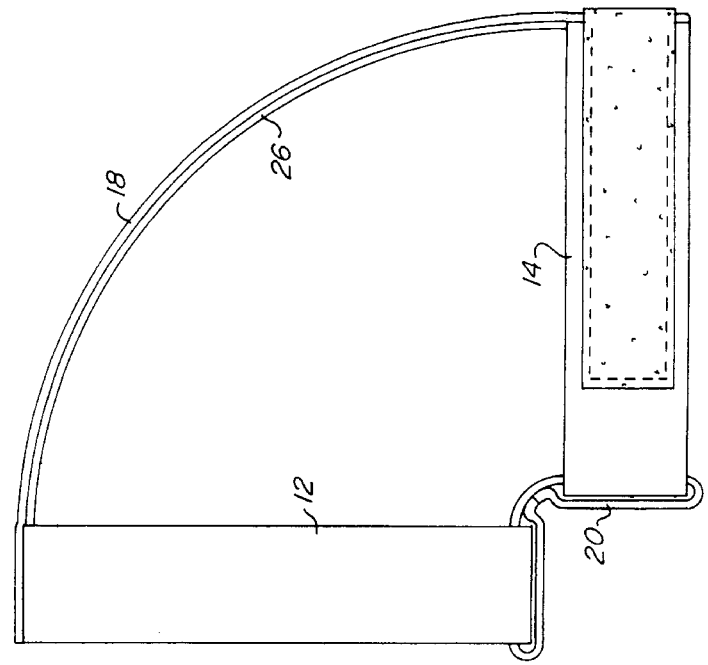

SUPPORT SYSTEM FOR CATHETER LEG BAG

BACKGROUND OF THE INVENTION

The present invention relates to support devices for urine collection bags used in conjunction with catheters and in particular to such devices designed to be supported on the leg of the user.

A number of support systems for urine catheter bags employ a plurality of (usually three) circumferential straps. Typically, however, the prior art devices disclose systems in which an upper circumferential strap encircles the waist of the user while two lower circumferential straps encircle the upper leg. Typical of these systems are U.S. Pat. No. 2,133,130, U.S. Pat. No. 4,073,295 and U.S. Pat. No. 3,897,785.

U.S. Pat. No. 2,133,130 issued to Buchstein on Oct. 11, 1938 for "Supra Pubic Drain Appliance" discloses a device worn from a belt about the waist of the user. A urine drainage bag is attached to the user by a pair of straps about the thigh. A similar device with a belt about the waist of the user and a pair of straps about the thigh to support a urine bag is disclosed in U.S. Pat. No. 4,073,295 issued to Laufbahn on Feb. 14, 1978 for "Catheter." A variation of this arrangement is disclosed in U.S. Pat. No. 3,897,785 issued to Barto, Jr. on Aug. 5, 1975 for "Harness for a Disposable Urinal." Barto, Jr. discloses a harness for supporting a urine collection bag by means of a sheet member draped along the user's leg. The sheet member is suspended from a belt about the user's waist and held about the user's leg with a pair of straps. None of these devices are designed to be worn solely on the leg of the user, therefore none of them show any recognition of the problems associated with supporting a urine bag from a user's leg. In particular, none of these patents disclose a longitudinal control strap.

Some patents of this type do, however, show support straps and a few of them show a pair of longitudinal support straps. Examples include U.S. Pat. No. 1,416,238 and U.S. Pat. No. 4,511,358. These patents, too, disclose devices designed to be supported from the waist of the user and the longitudinal straps are not used to provide control to prevent the bag from rotating on the leg of the user. U.S. Pat. No. 4,173,970 mentions, without detailing the structure, French Patent No. 1,445,658 which is said to disclose "a pouch for a urine bag with mounting straps for mounting the pouch on a person's leg." col. 1, lines 20–23.

Those who are restricted in their ability to ambulate find the wearing of urine collection bags to be a necessary but troublesome procedure. While numerous devices have been proposed for supporting urine bags on ambulatory individuals as described above, a seated individual is not amenable to the same type of support system utilizing waist belts. Devices supporting urine bags from the user's legs generally provide no proper support, especially for full bag. Furthermore, bags are likely to slip or slide from the user's leg. An additional problem occurs for those who have limited use of their hands. A bag that has fallen out of position is not only uncomfortable, and difficult to retrieve, but may actually represent a danger to the user—from the strain put on the catheter, for example. Furthermore, tightening the straps is no solution since the straps will interfere with blood circulation.

SUMMARY OF THE INVENTION

The present invention comprises a series of three circumferential straps with suitable padding and adjustable hook and loop closures. These three circumferential straps are held in proximity to one another by a first longitudinal strap connecting the three on their front surface, and a second longitudinal control strap between the upper strap and the second strap on their rear surfaces. The longitudinal control strap acts fundamentally as a hinge between the upper two circumferential straps to prevent the circumferential straps from twisting out of position relative to one another. The longitudinal control strap is only long enough to bridge the gap between the back sides of the upper two circumferential straps in position above and below the knee respectively of a seated user. The longitudinal strap, by contrast, fulfills a different function and is the primary load bearing strap.

The second circumferential strap and the lower, third strap have, upon their outer surfaces, loop closure material which matches hook closure material threaded through the support holes formed into the bag.

It is therefore an object of the present invention to provide for a support system for a catheter urine collection bag which may be safely and comfortably worn on the leg of the user.

It is a further object of the present invention to provide for a support system for a catheter urine collection bag which resists slipping or sliding out of position on the leg of the user.

It is an additional object of the present invention to provide for a support system for a catheter urine collection bag which is simple and economical in construction.

Further objects and advantages of the present invention will be apparent from the detailed description of the preferred embodiments consider in conjunction with the appended drawing as described following.

BRIEF DESCRIPTION OF THE DRAWINGS

FIG. 1 is a right elevational view of the support system on a user's leg.

FIG. 2 is a left elevational view of the support system on a user's leg.

FIG. 3 is an enlarged partial front elevational view of the support system on a user's leg.

FIG. 6 is a left side elevational view of the upper circumferential straps of the support system showing the relationship between the longitudinal strap and the longitudinal control strap as they would appear when placed in position on the user's leg.

FIG. 7 is a right side elevational view of the upper circumferential straps of the support system showing the relationship between the longitudinal strap and the longitudinal control strap as they would appear when placed in position on the user's leg.

FIG. 8 is a front elevational view of the upper circumferential straps of the support system as it would appear on the user's leg as shown in FIG. 3.

DETAILED DESCRIPTION OF THE PREFERRED EMBODIMENTS

Figure 4:
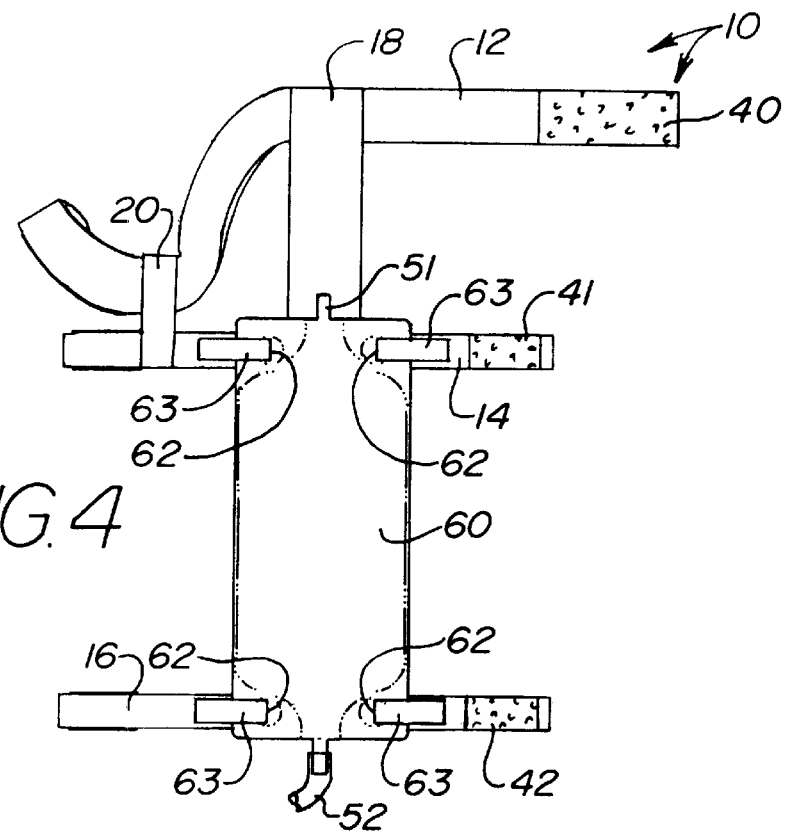
FIG. 4 is an enlarged front elevational view of the support system unfolded as it would appear prior to being placed in position on the user's leg.
Figure 5:
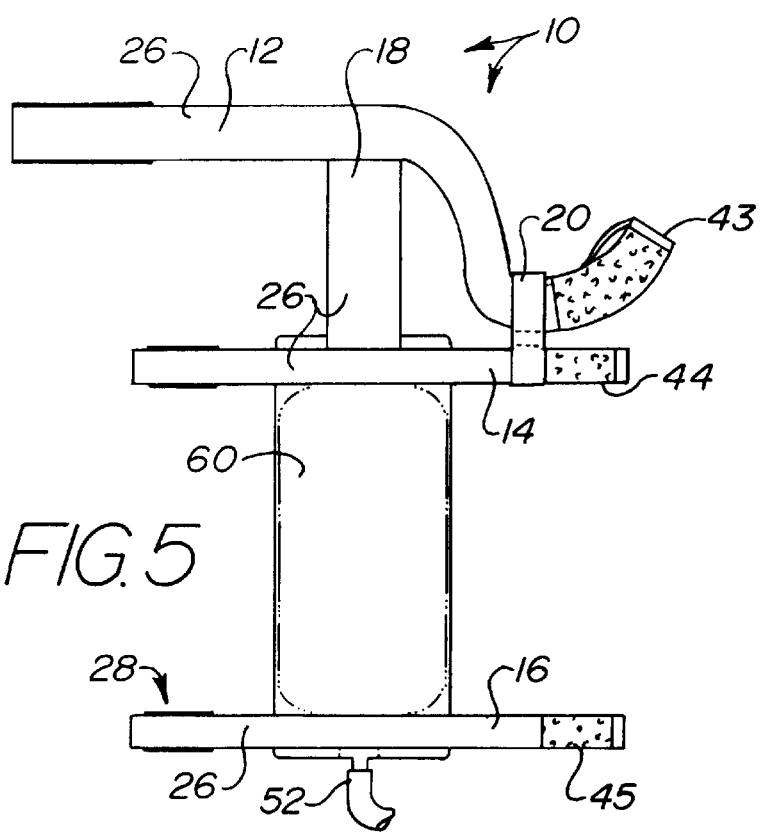
FIG. 5 is an enlarged rear elevational view of the support system unfolded as it would appear prior to being placed in position on the user's leg.

The support system 10 of the present invention may now be described with reference to the drawings. Particularly with reference to FIGS. 4 and 5, the preferred embodiment comprises a series of three circumferential straps which are placed so as to encircle the leg of the user—the first circumferential strap 12 encircles the leg of the user above the knee, the second circumferential strap 14 below the knee, and the third circumferential strap 16 above the ankle. These three straps are connected by a longitudinal strap 18 connected to the anterior of first circumferential strap 12, which is the principal weight bearing strap, and which is thence carried across the kneecap of the user, connected to the anterior of second circumferential strap 14, and terminates with its connection to the anterior of third circumferential strap 16. In an alternative embodiment, the longitudinal strap 18 may terminate at second strap 14 rather than continue to third strap 16.

Each of the circumferential straps 12, 14, 16 are provided with closures 22 which in the preferred embodiment are conventional hook and loop closures comprising hook portions 40, 41, 42 and loop portions 43, 44, 45, respectively located on respective opposite ends of circumferential straps 12, 14, 15 so that the respective straps fasten about the leg of the user on the inside of the leg. Additionally, the inside of the straps 12, 14, 16, 18 may be provided with padding material 26 for greater comfort to the user. Various types of suitable padding material are known in the art.

As shown in FIG. 3, the end of the first circumferential strap 12 is advantageously sewn over to provide a tubular pathway 24 for routing a catheter inlet tube 50 along the inside of the leg to the bag inlet 51.

The third circumferential strap 18, the lowest and therefore nearest the bag drain tube and pinch valve 52, has a hook and loop closure 28 on one end which allows the folded drain tube and pinch valve 52 to be retained in a stowed position until needed.

A longitudinal control strap 20 is attached to the respective posteriors of the first circumferential strap 12 and second circumferential strap 14. When worn by the user the longitudinal control strap 20 is positioned behind the knee of the user where the first and second circumferential straps 12, 14 are closest (when the user is seated with the knee flexed). The longitudinal control strap 20 is relatively short, only long enough to span the normal distance between the posteriors of the respective first and second circumferential straps 12, 14 when the user is seated. The longitudinal control strap 20 act therefore in the nature of a hinge between the first and second circumferential straps 12, 14 but due to its relatively short length prevents rotational shifting of the first circumferential strap 12 relative to the second circumferential strap 14. Ideally the first and second circumferential straps 12, 14 are maintained in a 70°–110° relationship to each other as viewed from the side relative to horizontal. This relationship may be described with reference to FIGS. 6, 7 and 8. This arrangement prevents the urine collection bag 60 from turning upon the user's leg.

The typical urine collection bag 60 is provided with support slots 62 at the top and bottom of the bag 60 for attachment to a suitable support. The second and third circumferential straps 14, 16 have straps 63 provided with hook and loop closures 30 which fit through the support slots 62 formed into the urine collection bag 60 and secure the bag top and bottom with the closures 30. When secured to the support system 10 and worn by the user, the bag 60 is disposed as shown on FIGS. 1, 2, and 3.

The weight of the bag 60 is transferred via the two longitudinal straps 18, 20 to the first circumferential strap 12, primarily by the longitudinal strap 18. The weight of the bag 60 is then born by the top of the leg behind the knee. The weight is then spread over an enlarged area by the width of the first circumferential strap 12 which as noted above may be padded. The longitudinal strap 18 also transfers a portion of the weight of the bag 60 to the kneecap of the user which helps to spread out the weight bearing task.

Alternately, the longitudinal strap 18 may end with its attachment to the second circumferential strap 14 since the third circumferential strap 16 is essentially non-weight bearing and serves mainly to keep the bottom of the bag 60 in close proximity to the leg of the user.

In one alternate embodiment, the entire support system 10, with the exception of the various hook and loop closures, is comprised of a single die-cut piece of neoprene wet-suit material. It retains all the features of the preferred embodiment, but lessens material cost and assembly time.

The present invention has been described with respect to certain preferred and alternative embodiments which are intended to be exemplary only and not limiting to the full scope of the invention as set forth in the appended claims.

What is claimed is:

1. In combination, a catheter urine collection leg bag and a support system for a catheter urine collection leg bag, comprising:

a first circumferential leg encircling strap for encircling the leg of the user above the knee;

a second circumferential leg encircling strap for encircling the leg of the user below the knee;

a third circumferential leg encircling strap for encircling the leg of the user above the ankle;

a longitudinal strap affixed to the anterior of said first strap and the anterior of said second strap;

a control strap affixed to the posterior of said first strap and to the posterior of said second strap and having a length whereby said posterior of said first strap and said posterior of said second strap are maintained in close proximity to prevent rotational shift of said first strap relative to said second strap;

means for removably attaching said catheter urine collection bag to said second strap and to said third strap.

2. The combination of claim 1 wherein said first strap, said second strap and said third strap each further comprise hook and loop fastening means for removably securing said first strap, said second strap, and said third strap to the leg of the user.

3. The combination of claim 2 wherein said catheter urine collection bag has support slots for attachment to a support and said means for removably attaching a catheter urine collection bag comprises hook and loop fastener straps affixed to said second strap and to said third strap and adapted for attachment to said catheter urine collection bag by means of the support slots.

4. The combination of claim 3 wherein said catheter urine collection bag has an inlet tube, further comprising means for securing said inlet tube to said first strap.

5. The combination of claim 4 wherein said catheter urine collection bag has a drain tube and pinch valve associated therewith, further comprising means on said third strap for securing the drain tube and pinch valve in a stowed position.

6. The combination of claim 5 where said longitudinal strap further comprises an extension from said second strap to said third strap.

7. The combination of claim 6 wherein said first strap, said second strap, said third strap, said longitudinal strap and said control strap comprise a single die-cut piece of neoprene wet-suit material.

* * * * *